(12) United States Patent
Omura et al.

(10) Patent No.: US 8,393,327 B2
(45) Date of Patent: Mar. 12, 2013

(54) HEADGEAR AND ITS MANUFACTURING METHOD

(75) Inventors: Keiko Omura, Hino (JP); Masahide Takishita, Hino (JP); Shin Ooya, Hino (JP); Tongoh Chin, Hino (JP); Hideharu Shimura, Osaka (JP); Shinya Fujimoto, Ibaraki (JP); Toru Hikosaka, Ibaraka (JP); Toshiki Nakamura, Chiyoda-ku (JP); Kazuaki Fujiura, Chiyoda-ku (JP); Naoki Kurai, Chiyoda-ku (JP)

(73) Assignee: Teijin Pharma Limited, Tokyo (JP)

( * ) Notice: Subject to any disclaimer, the term of this patent is extended or adjusted under 35 U.S.C. 154(b) by 873 days.

(21) Appl. No.: 12/517,751

(22) PCT Filed: Oct. 16, 2007

(86) PCT No.: PCT/JP2007/070504
§ 371 (c)(1),
(2), (4) Date: Jun. 4, 2009

(87) PCT Pub. No.: WO2008/068966
PCT Pub. Date: Jun. 12, 2008

(65) Prior Publication Data
US 2009/0250065 A1    Oct. 8, 2009

(30) Foreign Application Priority Data

Dec. 8, 2006  (JP) ................................. 2006-331958

(51) Int. Cl.
*A62B 18/08* (2006.01)

(52) U.S. Cl. ................................................. 128/207.11

(58) Field of Classification Search ........... 128/201.22–201.23, 205.25, 206.12, 128/206.21, 207.11, 207.17
See application file for complete search history.

(56) References Cited

U.S. PATENT DOCUMENTS 6,418,929 B1    7/2002   Norfleet
(Continued)

FOREIGN PATENT DOCUMENTS

| JP | 2000-254229 A | 9/2000 |
| JP | 2003-299744 A | 10/2003 |

(Continued)

OTHER PUBLICATIONS

Supplementary European Search Report EP 07 83 0238; Jul. 23, 2012.
Taiwan Patent Office Action Appln. No. 10121022710 Sep. 26, 2012.

*Primary Examiner* — Kristen Matter
(74) *Attorney, Agent, or Firm* — Sughrue Mion, PLLC

(57) ABSTRACT

A headgear suitable for wearing a respiratory mask system wearing on the head of a user is provided, wherein it can be easily manufactured, the leakage of the positive pressure gas when pressurized is reduced, and a good wearing feel is achieved. The headgear is adapted to secure a respiratory mask, which contacts the face of the user to supply a positive pressure gas for respiration to the user, to the head of user. The headgear has a head mounted portion which is worn on the occipital of the user and a strap (3) connecting to this head mounted portion. The head mounted portion has at least one closed curved belt (1) which has thereon at least one junction (2). At least one junction provides the closed curved belt with a nonplanar structure adaptable to the shape of the head of the user.

14 Claims, 7 Drawing Sheets

U.S. PATENT DOCUMENTS

| | | | |
|---|---|---|---|
| 6,422,238 B1 * | 7/2002 | Lithgow | 128/207.11 |
| 2003/0196655 A1 | 10/2003 | Ging et al. | |
| 2004/0149280 A1 | 8/2004 | Semeniuk | |
| 2006/0283461 A1 | 12/2006 | Lubke et al. | |
| 2007/0175480 A1 * | 8/2007 | Gradon et al. | 128/207.11 |
| 2008/0110466 A1 * | 5/2008 | Armitstead | 128/207.11 |
| 2010/0000539 A1 * | 1/2010 | Woodard et al. | 128/205.25 |
| 2012/0017912 A1 * | 1/2012 | Ging et al. | 128/207.11 |
| 2012/0024290 A1 * | 2/2012 | Amarasinghe et al. | 128/207.11 |

FOREIGN PATENT DOCUMENTS

| | | |
|---|---|---|
| JP | 2004-000570 A | 1/2004 |
| TW | 482690 | 4/2002 |
| WO | 2006/000046 A1 | 1/2006 |
| WO | 2006072128 A1 | 7/2006 |
| WO | 2006130903 A1 | 12/2006 |
| WO | 2007006089 A1 | 1/2007 |

* cited by examiner

HEADGEAR AND ITS MANUFACTURING METHOD

TECHNICAL FIELD

The present invention relates to a headgear which is used for securing a respiratory mask, to the head of a user, which is used in a CPAP (Continuous Positive Airway Pressure) therapy suitable for the treatment of sleep apnea syndrome, or an NIPPV (Nasal Intermittent Positive Pressure Ventilation) therapy suitable for treatment of ventilatory insufficiency and the like and a manufacturing method for the headgear.

BACKGROUND ART

Continuous Positive Airway Pressure (CPAP) is one of the most effective treatments for sleep apnea syndrome. This treatment utilizes respiratory equipment providing a positive pressure gas in the range of 400 to 2000 Pa in the nostrils, or the nostrils and the mouth, or the face of a user during sleep. Further, Nasal Intermittent Positive Pressure Ventilation (NIPPV) is one of the most effective treatments for ventilatory insufficiency, utilizing respiratory equipment providing an intermittent positive pressure gas in the range of 400 to 2400 Pa in the nostrils of a user.

As respiratory used in these therapies, there are nasal masks providing a positive pressure gas in the nostrils under pressure, full-face masks providing the positive pressure gas holding the nostrils and the mouth, and total face masks providing the positive pressure gas over the entire face.

These respiratory masks are secure to the head of a user by a strap portion connected to a head mount of a headgear worn in the proximity of the opistocranion of the head of the user (JIS Z8500, ISO 7250).

When performing treatment using the above stated equipment, in order to provide a continuous positive pressure gas to the nostrils and the like of a user generally, the respiratory mask is comprised of an elbow connecting a hose guiding the positive pressure gas for respiration, a frame connecting with the elbow to hold a mask cushion in a specified position, and a hollow mask cushion which is closely attached to the face of a user. Such a respiratory mask is closely attached to the face of a user by the tension of the stretchable strap portion of the headgear (for example, see Japanese Patent Kokai No. 11-000397; Pamphlet of International Publication No. WO01/097893, and Pamphlet of International Publication No. 98/04310).

However, once, the respiratory mask is normally installed, it is known that displacement of the mask cushion occurs due to various causes while wearing. Because of that, measures have been taken which prevent or reduce the displacement corresponding to the respective causes. For example, to this end, a bellows is provided between the frame portion and the face contact portion of the mask cushion, in the nasal respiratory masks described in Japanese Patent Kokai No. 11-000397 and Pamphlet of International Publication No. WO 01/097893 to prevent an influence on the mask cushion from the displacement of the frame portion which occurs by contact with bed clothing. Further, in a respiratory mask described in Pamphlet of International Publication No. WO 96/17643, a flexible material is used for the wall around the connection portion of the positive pressure gas supply hose in order to reduce the displacement of the frame portion caused when it is pulled by the positive pressure gas supply hose connected to the frame.

Such a displacement causes the supplied positive pressure gas to leak, from the boundary between the mask cushion and the face, giving discomfort, irritation to the ocular region, and chills and the like to the user due to gas leaks, and depending on the case treatment is obliged to be discontinued. The gas leakage from the mask cushion in such conventional technology remarkably takes place in the root of nose region, nasal alae region and the like. For preventing such gas leaks, there is but one method which further strongly tightens the belt for securing a respiratory mask regardless of the location of the leak, but it is indicated that when wearing all night long for a long period of time during sleep and the like, it is possible that a respiratory mask can harm the face of a user.

DISCLOSURE OF THE INVENTION

Problems to be Solved by the Invention

However, in any one of the aforementioned technologies, the wearing of the headgear is necessary to secure the respiratory mask. Here, in order to adapt the headgear to the head of a user, if the material used in the headgear stretches easily, when it is pressurized, the headgear stretches too much, the respiratory mask rises up, and creates leakage of the positive pressure gas. Further, if a user lying down turns his or her body, the members forming the headgear are stretched by the weight of the respiratory mask, and hence, the respiratory mask is displaced, thus creating the leakage of the positive pressure gas.

However, if using a material which is difficult to stretch for the headgear, adjustability to the shape of the head of a user becomes poor, and it contacts with the head only in the peripheral edges of each surface of the headgear. Therefore, there are the problems where the head becomes locally compressed, and when a respiratory mask is worn for a long period of time, pain occurs.

Further, if the surface of a portion of the headgear rises up, catching on the pillow and other bed clothing, the displacement of headgear and accordingly the respiratory mask may occur.

Namely, the problems remaining unresolved before the filing of the present application and to be resolved by the present invention are to satisfy both the requirements of the prevention of leakage of the positive pressure gas arising in the headgear and alleviation of the compression sensation by the headgear.

Means to Solve the Problems

According to the present invention, there is provided a headgear for securing a respiratory mask to a head of a user, wherein the respiratory mask contacts a face of the user to supply a positive pressure gas for respiration to the user, the headgear comprising: a head mounted portion which is mounted on the occipital of the user, and a strap connecting to the head mounted portion, said head mounted portion having at least one closed curved belt, said closed curved belt having thereon at least one junction, at least one of the junctions provides the closed curved belt with a nonplanar structure adaptable to a shape of the head of the user.

According to another aspect of the present invention, there is provided a method of manufacturing a headgear mentioned above comprising: cutting off step to cut off a member forming a closed curved belt portion from a planar material, and connecting step to connect at least one pair of a first cut end and a second cut end in the cut out member to form at least one junction, wherein, in said cutting off step, a series of members forming the closed curved belt portion are cut off from the planar material; at least one place of the portion of the series of members corresponding to the closed curved belt portion is cut off along a first cutting line, and is further cut off along a second cutting line which is in the proximity of the first cutting line and is not parallel with and does not intersect the first cutting line, to form said at least one pair of first cut end and second cut end, or, each of the members forming said closed curved belt portions having said at least one pair of first cut end and second cut end is individually cut off from one or more planar materials.

Here, the "head mounted portion" is the portion of the headgear that is secured to the periphery of the opistocranion of the head of a user by the tension of the strap. Namely, the head of the user is placed between the head mounted portion and the respiratory mask, and when both the head mounted portion and the mask are pressed against the head of the user by the tension of the strap, they are secured to the head of the user.

Consequently, the strap of the headgear of the present invention is secured at its one end to the head mounted portion, and can be secured at the other end to the respiratory mask.

The headgear of the present invention for securing a respiratory mask has advantages, that even the headgear using a clothing fabric which is difficult to stretch can prevent the leakage of the positive pressure gas because it possesses a stereoscopic structure which adapts to the shape of the head of a user, and that a good wearing feel can be maintained.

Further, because the headgear of the present invention for securing a respiratory mask possesses a stereoscopic structure which adapts to the shape of the head of a user, even when the headgear touches pillows or other bed clothing, the headgear is hardly caught thereby, and as a result, it is possible to prevent the respiratory mask from moving.

According to the present invention, there is also the advantage of obtaining these effects at a low cost.

BEST MODE TO CARRY OUT THE INVENTION

The headgear of the present invention has a head mounted portion which is worn on the occipital of a user and a strap connected thereto.

As the material for the headgear of the present invention, for example, synthetic resin, fabric and the like can be used, but the effect of the present invention is difficult to obtain in an excessively stretchable material. For example, it is necessary to appropriately adjust the thickness and width, etc., of stretchable materials such as polyurethane foam, neoprene rubber, jerseys and make it difficult to stretch to some extent. Specifically, among the head mounted portion and the strap portion, it is desirable to produce at least the strap portion by the material where the stretch when pulled at 1.96 N is 0.05% to 20%, preferably 1% to 10%. If using this kind of material, the leakage of the positive pressure gas can be reduced, and, the wearability of the mask improves. If a material whose stretch when pulled at 1.96 N is larger than 20%, is used, leakage of the positive pressure gas may occur, and if a material whose stretch when pulled at 1.96 N is smaller than 0.05% is used, the adjustability to the shape of the head of a user is poor, and, when the respiratory mask is worn over a long period of time, there is the possibility of causing pain.

Such a head mounted portion possesses at least one belt defined by a closed curve. If only to achieve the function of the headgear to secure a respiratory mask to the head of a user via the strap portion, the head mounted portion may be planar, but in fact, for the sake of providing air permeability to prevent sweating and weight savings and the like, it can use a closed curved belt shape in which the center portion is hollow. If one is skilled in the art, it is possible to decide the width of such a belt-like portion as needed, considering the stretchability, thickness, wearing feel, weight, cost and the like of the belt-like portion. If the width is too wide, generally, the weight and cost increase, and stretchability decreases. If the width is too narrow, the pressure to the head is concentrated in a narrow region and wearing feel deteriorates. If it is necessary, performing optimization experimentation can determine a specific numerical value. Additionally, it is not necessary for the width of the belt-like portion to be the same over the entire circumference of the closed curve.

Figure 5:
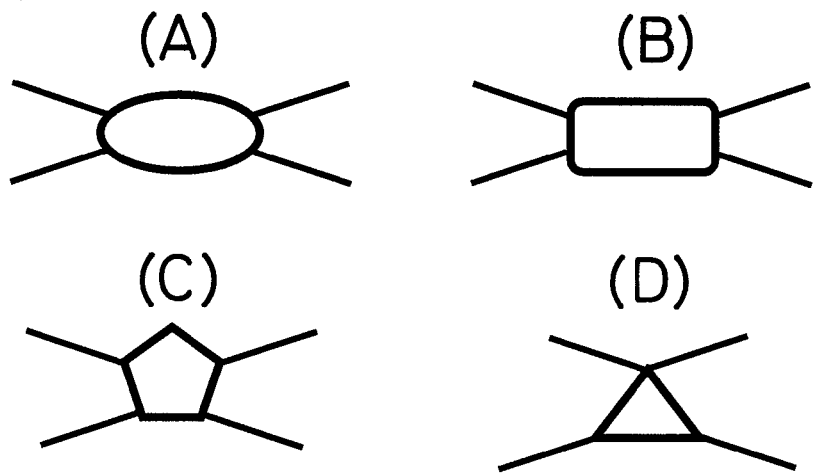
FIG. 5 schematically shows examples of the head mounted portion and strap in the headgear of the present invention.

Provided that the function of the present invention is achieved, the shape of such a closed curved belt has no specific limitations, but for example, it is possible to make the shapes circular, elliptical or polygonal such as isosceles triangular and rectangular such as regular polygonal, equilateral triangular or squares or analogous shapes. Specifically, it is preferable that the shape of the closed curved belt is generally circular, elliptical, or regular polygonal, because the shape balance is good and it is easy to adjust the center of the closed curved belt to the opistocranion of the head of a user. Examples of the head mounted portion and the strap are typically shown in FIG. 5. In FIG. 5, (A) shows the shape of the closed curved belt being generally elliptical, (B) shows the shape of the closed curved belt being generally rectangular, (C) shows the shape of the closed curved belt being generally regular pentagonal, and (D) shows the shape of the closed curved belt being generally regular triangular.

Such a closed curved belt possesses at least one junction which provides a nonplanar structure to the closed curved belt corresponding to the shape of the head of a user. When such a junction is provided, the end parts of the member forming the closed curved belt preferably do not overlap. This is because a step which causes catching on pillows and other bed clothing is not created.

This kind of junction can be produced by various connection methods such as stitching, thermal adhering, the use of adhesive agents, or the use of hook-loop material (known as Velcro™), but among them, producing by stitching is preferable from the viewpoint of manufacturability, wearability and durability. Consequently, the junction produced by stitching is explained below, but the present invention is not limited to this.

The cut portion (including the first cut end and the second cut end in the present invention) of such a closed curved belt, generally, is linear, but if the stitching does not cause displacement, and as far as a clearance gap is not created when the cut portions are stitched and the object of the present invention can be attained, other curved lines are also possible.

The number of the stitched portions contributing to making such a nonplanar structure, can be either one or plural. The greater the number of the stitched portions, the more likely it is able to be adjusted to the shape of the head of a user, on the other hand, the labor in the manufacturing process increases. Consequently, two stitched portions contributing to making a nonplanar structure are typically provided. Further, if significance is placed on manufacturability, it is preferable that one stitched portion contributing to making a nonplanar structure is provided.

Though, it is possible that the headgear of the present invention, other than the stitched portion which provides the closed curved belt with a nonplanar structure, for example, for the convenience of the manufacturing process, further possesses a stitched portion which does not contribute to making the nonplanar structure. For example, four stitched portions are provided wherein, every other two portions are used to make the nonplanar structure, and the other two portions do not contribute to making the nonplanar structure. The presence of four stitched portions is suitable for manufacturing the headgear of a four strap structure which when worn has an especially superior balance.

When the stitched portion providing the nonplanar structure in the present invention is linear, it is possible to design the open angle to adapt to the shape of the head of a user, but when a user has the shape of a Japanese person's head, it is preferable that the sum of such open angles is 15 degrees or more. Here, the "open angle" is the angle defined by "the first cut line" (for example, the dashed lines P and S in FIG. 3) and "the second cut line" (for example, the dashed lines Q and R in FIG. 3), or is the angle defined by "the first cut end" (for example, the end of the belt along the dashed lines P and S in FIG. 3) and "the second cut end" (for example, the end of the belt along the dashed lines Q and R in FIG. 3), which will be explained hereinafter in connection with the manufacturing method of the headgear of the present invention.

Figure 6:
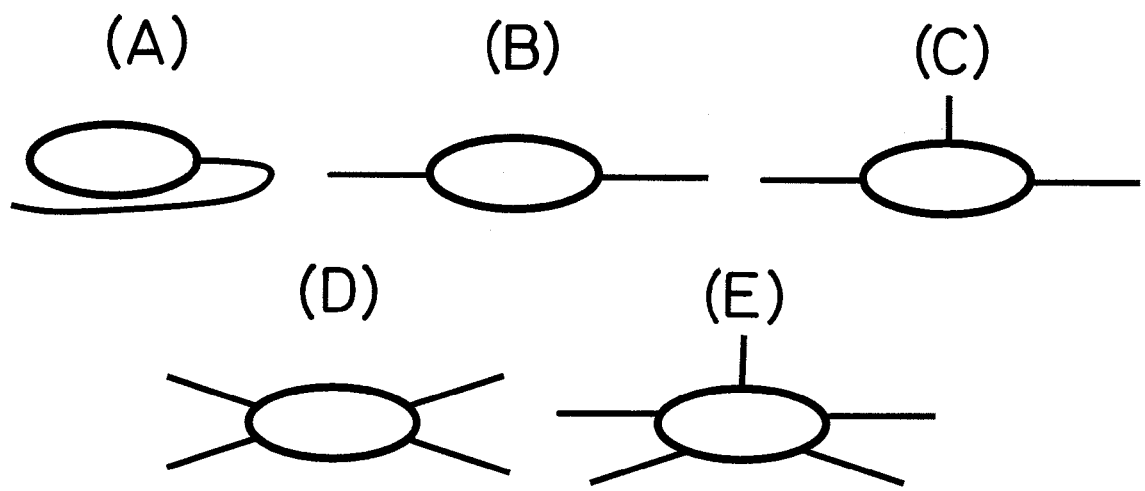
FIG. 6 schematically illustrates the number of straps and the attachment positions in the headgear of the present invention.

Provided that the strap portions in the headgear of the present invention bring about the effect of the present invention there are no restrictions in the number thereof, but there are generally 1 to 5 straps. Here, in order to explain examples of the attachment positions of the strap portions to the head mounted portion and the number thereof, examples of the structure of the head mounted portion and the strap portion are typically shown in FIG. 6. In FIG. 6, (A) shows one strap provided, (B) shows two straps provided, (C) shows three straps provided, (D) shows four straps provided, and (E) shows five straps provided. Among these, it is preferable that four straps are provided as is specifically shown in FIG. 6 (D), because when the headgear is worn on the head of a user, a superior balance can be obtained, and manufacturing is also easy. Additionally, if there is one strap as shown in FIG. 6 (A), the one end is secured to the head mounted portion and, the other end extends through a respiratory mask, and is connected to a portion of the headgear via a connector and the like.

It is possible to manufacture the strap portion in the headgear of the present invention integrally with the aforementioned closed curved belt or it is possible to secure the strap portion produced separately from the closed curved belt to the closed curved belt. The tip of the strap portion is usually processed so that it can be suitably secured to the frame portion and the like of the respiratory mask. For example, it is connected to one of the connectors.

Figure 7:
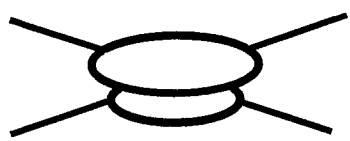
FIG. 7 schematically illustrates the headgear of the present invention in which another annular structure is added to the head mounted portion.
Figure 10:
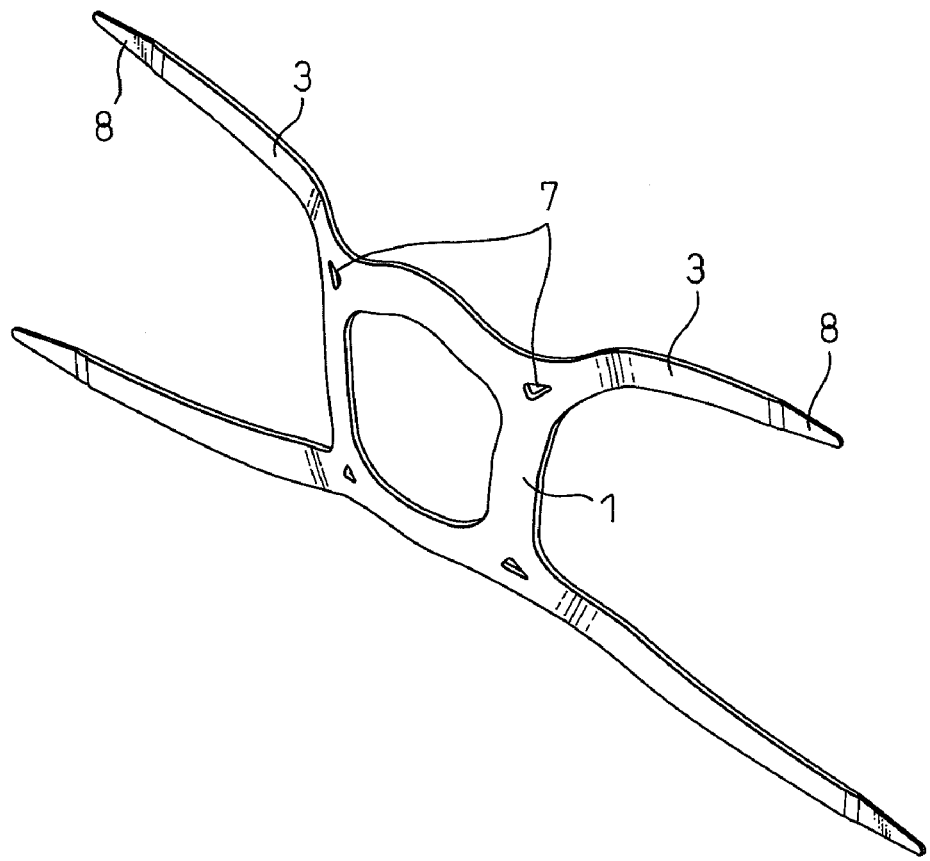
FIG. 10 is a perspective view of an example of the headgear of the present invention.
Figure 11:
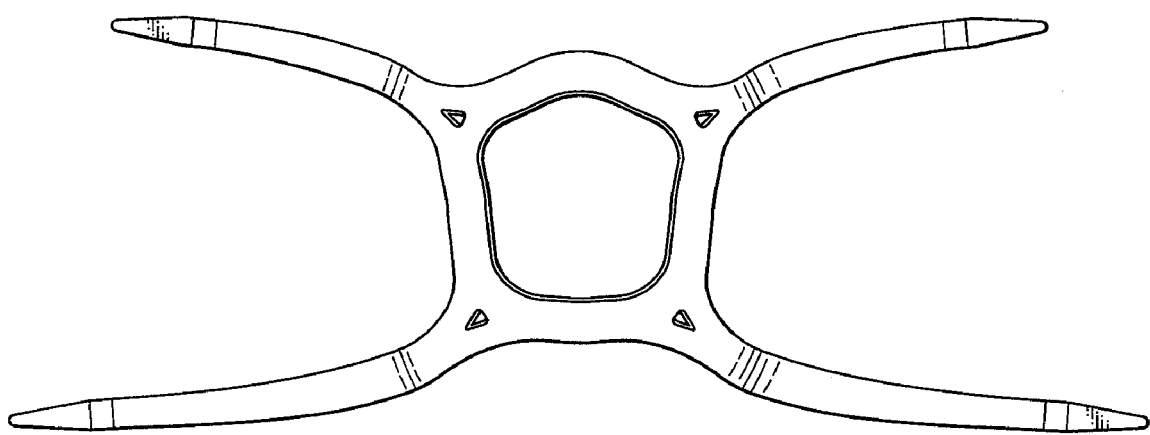
FIG. 11 is a front view of one example of the headgear of the present invention.
Figure 12:
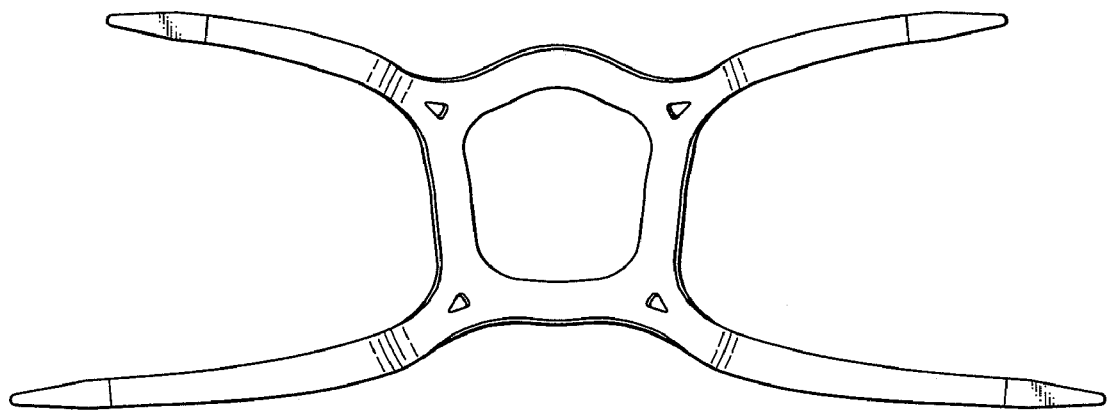
FIG. 12 is a back view of an example of the headgear of the present invention.
Figure 13:
FIG. 13 is a right side view of an example of the headgear of the present invention.
Figure 14:
FIG. 14 is a plan view of an example of the headgear of the present invention.
Figure 15:
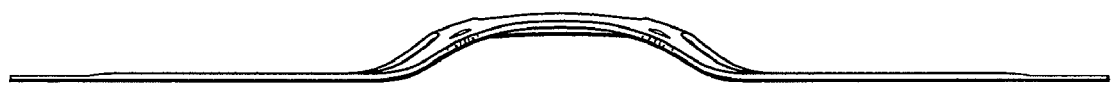
FIG. 15 is a bottom view of an example of the headgear of the present invention.

The headgear of the present invention may have a structure other than the closed curved belt and the straps. For example, as shown in FIG. 7, another annular structure maybe provided in contact with the closed curved belt. Further, for the purpose of the adjustment of the tension of each portion and the release of humidity, it is possible to provide holes (for example, see reference numeral 7 in FIG. 10) in the closed curved belt and/or the strap in accordance with need.

Figure 8:
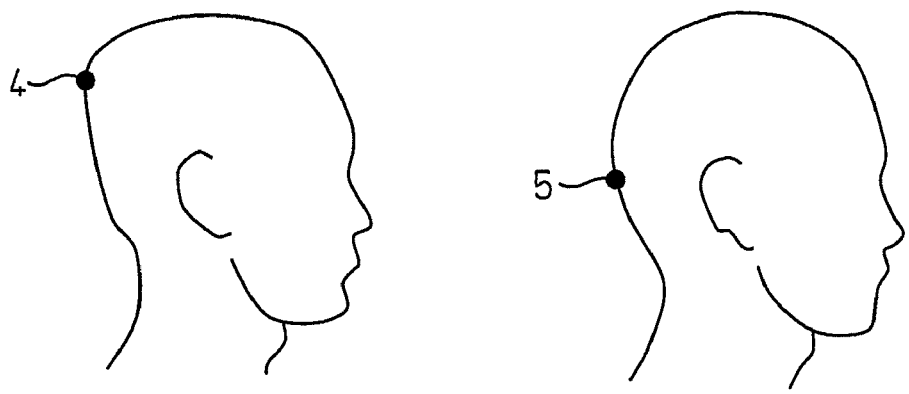
FIGS. 8(A) and (B) compares the characteristics of head shapes of Western and Japanese persons.

One preferred embodiment of the headgear of the present invention provides the headgear which possesses a structure suitable for the shape of the head of a Japanese person. For example, as shown in FIGS. 8(A) and (B), generally, the head of a Western person is such that the opistocranion (4) lies in a high position and the peripheral slope is steep, and the head of a Japanese person is such that the opistocranion (5) is low and the peripheral slope is gradual. Consequently, if a Japanese person uses a headgear suitable for the shape of the head of a Western person, namely, a headgear in which the area of the closed curved belt is small or the position of the closed curved belt lies in a relatively high position, because the closed curved belt tends not to engage with the opistocranion of the head of a Japanese person, this results in the occurrence of positional deviation. Note that, the user is referred to simply as Japanese person for the clarity of the explanation in the specification, but it goes without saying that the user is not limited to Japanese people and the headgear of the present invention can be appropriately used with any person, possessing a head structure close to the head structure of a Japanese person.

The headgear of the present invention suited for the head structure of such a Japanese person is, specifically, the headgear possessing four straps of which, two straps have a linear distance from the center of the closed curved belt to the ends of the straps of 35 cm to 45 cm (for example, 40 cm), and the remaining two straps have a linear distance from the center of the closed curved belt to the ends of the straps of 28 cm to 38 cm (for example, 33 cm).

Figure 9:
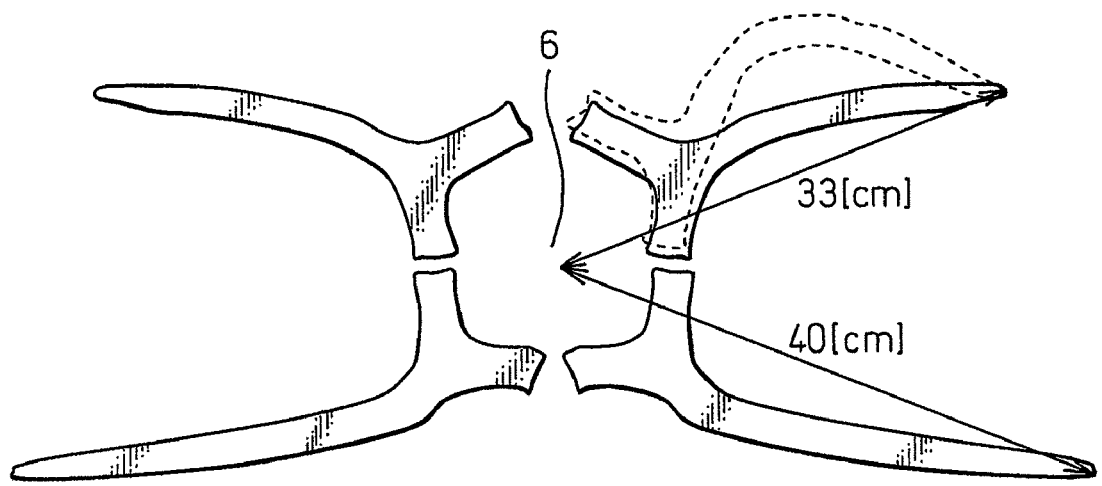
FIG. 9 shows an example of the headgear of the present invention suited for the head shape of a Japanese person.

Here, "the center of the closed curved belt" is, for example, as shown in FIG. 9, when it is assumed that the opening defined and surrounded by the closed curved belt is a flat plate, the point (6) corresponding to the center of the flat plate.

Further, in another preferred embodiment of the headgear of the present invention, suitable for the head structure of a Japanese person, the center of the closed curved belt is positioned on the opistocranion of the head of a Japanese person when the headgear is worn, and the area defined and surrounded by the closed curved belt is 50 $cm^2$ to 120 $cm^2$.

It is possible to refer to the standard human head model of Japanese persons, or to the statistic (AIST) data which are the of the head sizes of Japanese persons to determine the opistocranion of the head of a Japanese person. Note that, during the actual wearing, it is acceptable for the position of the opistocranion and the center of the closed curved belt to have some minor deviations because there is practically no great influence on the effect of the headgear of the present invention.

Here, the area defined by the surrounding closed curved belt is determined to be 50 cm$^2$ to 120 cm$^2$, in order to wrap the slope near the opistocranion which is more gradual than Western persons.

Furthermore, the present invention is directed to a manufacturing method of a headgear. Namely, the manufacturing method of the headgear of the present invention includes, a cutting off step to cut off the member forming the closed curved belt portion (for example, see reference numeral 1 in FIG. 2) from a planar material, and a connecting step to connect at least one pair of first cut end and second cut end of the cut off member, to thereby form at least one junction.

Here, "member forming the closed curved belt portion" when the aforementioned closed curved belt portion and the strap portion are integrally manufactured, means the member (for example, the four blanks of an approximately Y-shape in FIG. 1) having the closed curved belt portion and the strap portion, and when possessing the structures other than the closed curved belt and the strap, it means the member containing the structures, and when the closed curved belt portion and the strap portion are separately manufactured, it means the member containing only the closed curved belt portion. Further, "one pair of first cut end and second cut end", means a pair of ends of the member forming the closed curved belt portion to produce, for example, the junctions as indicated at 2 in FIG. 2. Connecting the pair of cut ends produces the closed curved belt of the nonplanar structure adapted to the shape of the head of a user.

The cutting off step is specifically explained below. In the first method, a series of members forming the closed curved belt portion are cut off from a planar material; and at least one place of the portions of this series of material corresponding to the closed curved belt portions is cut off (the first cutting) along the first cutting line, and furthermore, is cut off (the second cutting) along the second cutting line which is in the proximity of the first cutting line and is not parallel with and does not intersect the first cutting line, to form at least one pair of a first cut end and a second cut end. Though, the first cutting and the second cutting are expressed mainly for convenience sake, in fact, it is preferable to perform the two cuttings simultaneously.

Here, "a series of members forming the closed curved belt portions" refers to a series of members possessing the closed curved belts of a planar structure, and when the closed curved belt portion and the strap portion are integrally manufactured as mentioned above, it means a series of members including the closed curved belt portions and the strap portions, and when a structure other than the closed curved belt and the strap is provided, it means a series of members including this structure, and when the closed curved belt portions and the strap portion are separately manufactured, it means a series of members including only the closed curved belt portions.

The first cutting line usually is a straight line.

On the other hand, the second cutting line must a) be in proximity to the first cutting line,
b) not be parallel with the first cutting line,
c) not intersect with the first cutting line, and
d) be obtained by sewing the corresponding cut ends together without overlapping to form the closed curved belt adapted to the shape of the head of a user.

The meaning of "in proximity" refers to the range which does not generate the waste of material by excessive chipping, but the range is not significant as long as the headgear of the present invention can be obtained. Generally, the second cutting line begins from one end of the first cutting line. If the second cutting line is parallel with the first cutting line, stitching of the cut ends does not provide the closed curved belt with the nonplanar structure. If the second cutting line intersects the first cutting line, it is not possible to sew together the corresponding cut ends over the entire length.

In a second method of the cutting off step, each of the members forming the closed curved belt portion having at least one pair of a first cut end and a second cut end is individually cut off from one or more planar materials. In this second method, the members can advantageously be cut off from small planar materials, and, a cost decrease can be expected by the application of the materials which are left over. Furthermore, compared to the aforementioned first method in which the member forming the closed curved belt portion is cut off from a large planar material, the amount of waste of the cut material can be reduced, and the manufacture equipment can be of a small size, yielding various merits in regards to manufacturing.

Figure 3:
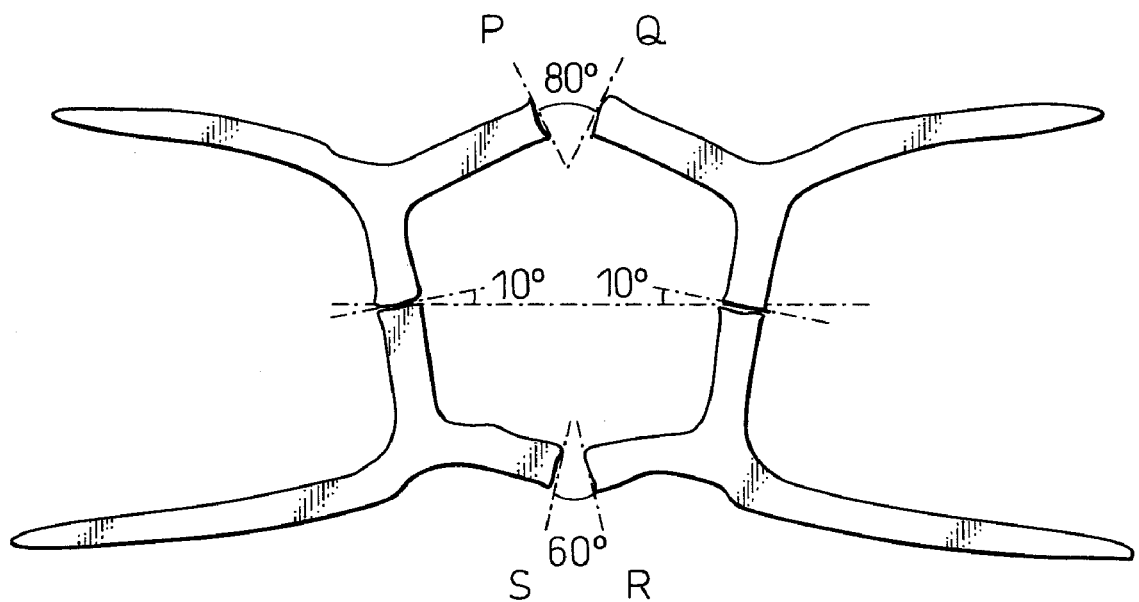
FIG. 3 shows one example of the headgear of the present invention before stitching.

In the cutting off step, it is preferable to produce at least one pair of a first cut end and a second cut end with the sum of the open angles of the first cut end and the second cut end being 15 degrees or more when the member forming the closed curved belt portion lies in plane. Thus, it is possible to make the three dimensional shape of the closed curved belt adaptable to the shape of the head of a Japanese person. For example, as shown in FIG. 3, when the angles of the first cut end and the second cut end from the tangential direction to the closed curve are respectively 60 degrees and 120 degrees, 50 degrees and 130 degrees, the cut ends respectively form the open angles of 60 degrees and 80 degrees (total 140 degrees) on a plane. The above-mentioned open angles make the headgear adaptable to the shape of the head of a Japanese person satisfactorily.

EXAMPLES

Below, specific examples of the present invention are further explained in detail with reference to the drawings.

Example 1

Figure 1:
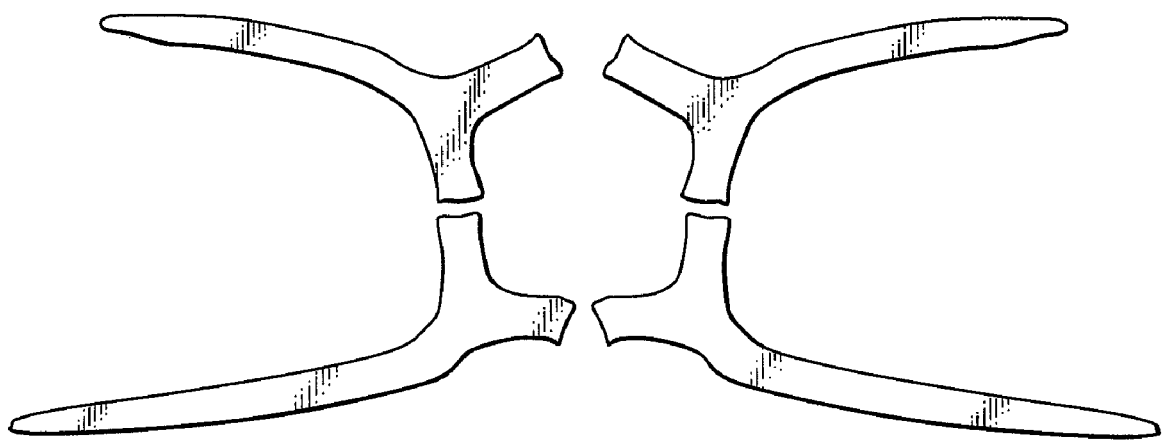
FIG. 1 shows one example of the headgear of the present invention before stitching.
Figure 2:
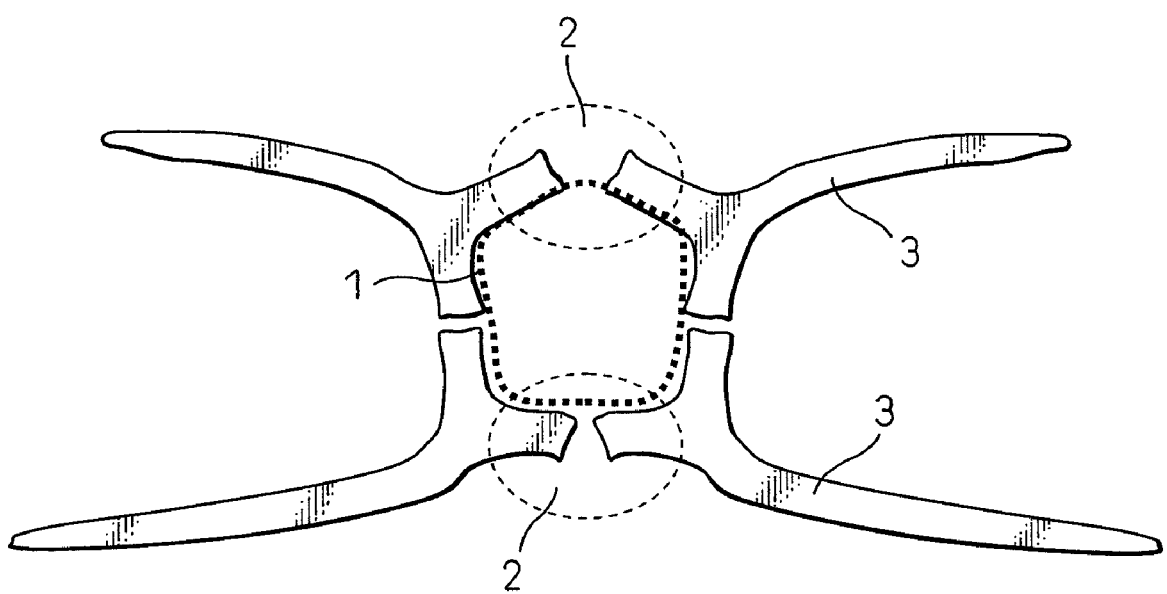
FIG. 2 shows one example of the headgear of the present invention before stitching.
Figure 4:
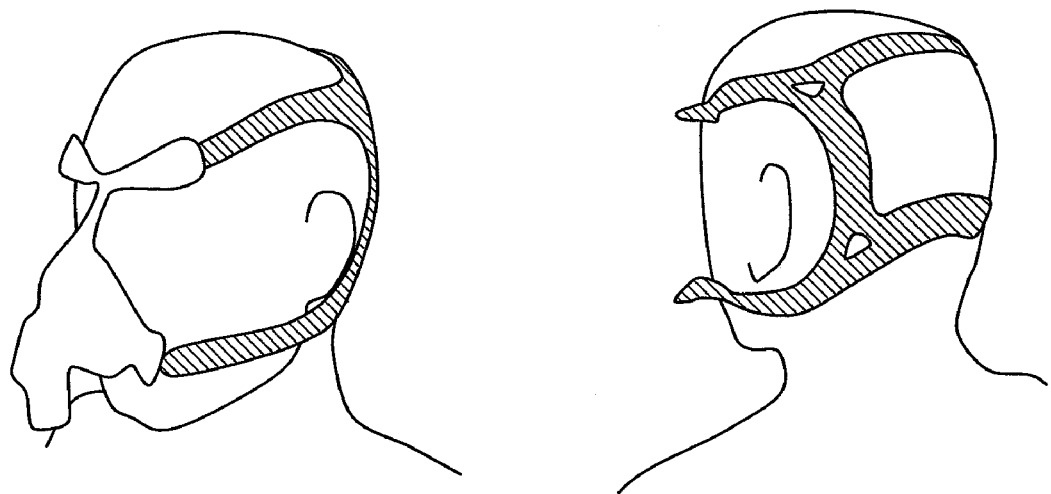
FIG. 4 shows the headgear of the present invention, worn by a user.

FIG. 1 shows four members (which form the closed curved belt portion) before the stitching to manufacture one example of the headgear of the present invention. If arranged as shown in FIG. 1, the "closed curved belt" portion as indicated by the dashed line (1) in FIG. 2, can be conceived. When the stitched portions (2) providing the nonplanar structure to the closed curved belt in FIG. 2 are arranged on a plane, the gap between the opposed ends is larger on the peripheral side of the closed curved belt than on the inner peripheral side. When all of the four stitched portions are stitched, the closed curved belt of the nonplanar structure is obtained. In FIG. 3, the angles of the stitched portions are illustrated. FIG. 4 shows a user wearing the headgear of the present invention.

Example 2

As shown in FIGS. 8(A) and 8(B), generally, the head shapes of Western and Japanese people are different. In FIG. 9, one example of the headgear of the present invention having four straps suitable for the head shape of a Japanese person is shown. Here, it is assumed that the center (6) of the closed curved belt is identical to the opistocranion of the head of a user. Here, the distance from the center (6) of the closed curved belt to the ends of the straps is defined but the length of the strap itself does not matter. Further, there are no restrictions regarding the shape of the strap as long as it is practicable. For example, the shape as indicated in FIG. 9 by the dashed line can be used.

Example 3

Figure 16:
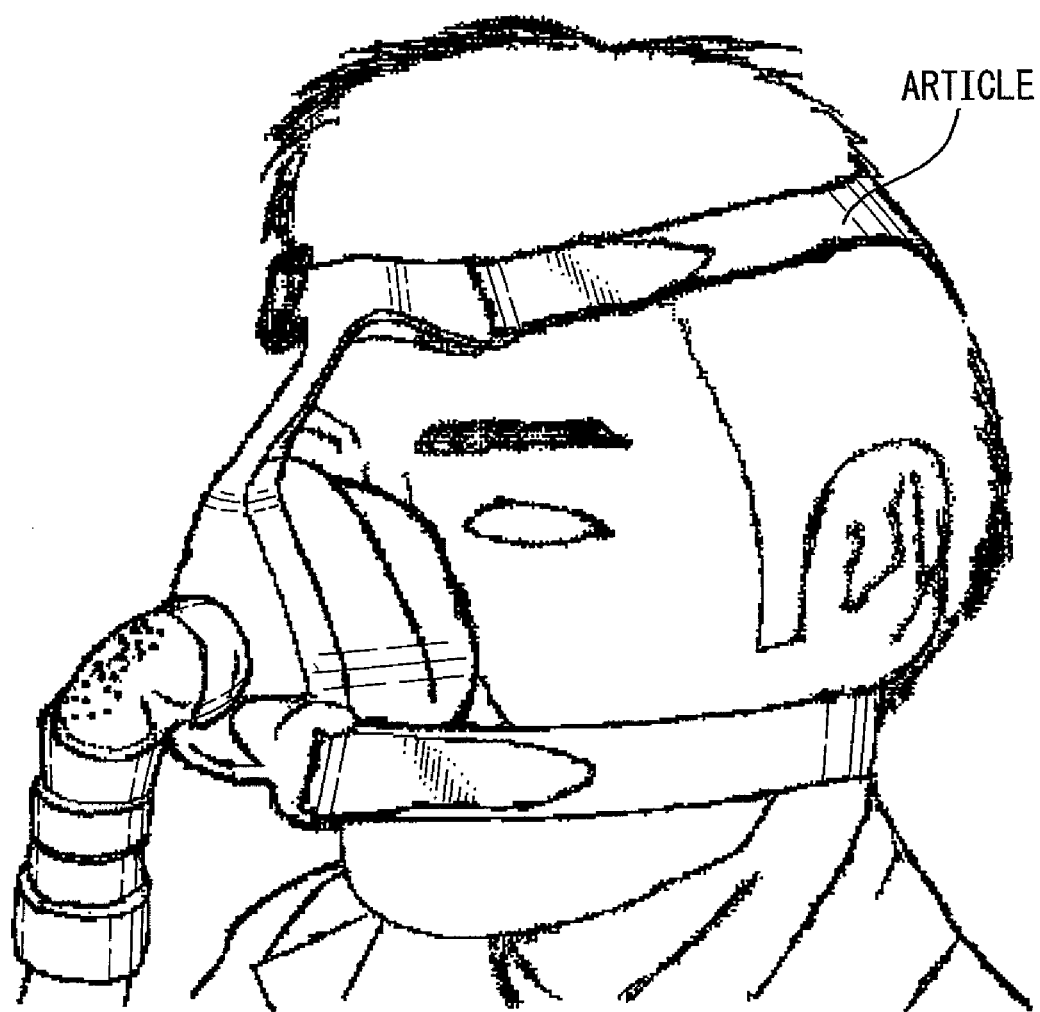
FIG. 16 is an explanatory view showing an example of the headgear of the present invention in use.

Another example of the headgear according to the present invention is shown in FIGS. 10 to 15, in which the headgear (wearing belt for respiratory mask) is provided with four holes (7) in the closed curved belt portion (1) for the purpose of the adjustment of the tension of each portion and the release of the humidity. In this headgear, the shape of the closed curved belt portion (1) is generally equilateral pentagonal and four straps (3) are provided. A Hook-and-Loop fastener portion (8) is provided at the tip of each strap (3). Consequently, for example, as shown in FIG. 16, the tip of each strap (3) extends through the strap mounting hole of the nasal mask frame, and the intermediate portion of each strap (3) is folded back to attach the Hook-and-Loop fastener portion (8) to the surface of each strap (3), so that the nasal mask can be secured to the head of a user. Note that, in FIGS. 10 to 15, the junctions of the closed curved belt portion (1) are not shown, but naturally, this headgear possesses the junctions in the necessary places. Further, in FIG. 13, only the right side view is shown, and the left side view is not shown because the right side view and left side view are symmetrical.

INDUSTRIAL APPLICABILITY

According to the present invention, a headgear which is used to secure a respiratory mask used in CPAP therapy or NIPPV therapy, etc., to the head of a user is provided.

The invention claimed is:

1. A headgear for securing a respiratory mask to a head of a user, in use, wherein the respiratory mask contacts a face of the user to supply a positive pressure gas for respiration to the user, the headgear comprising:
   a head mounted portion which is mounted on the occipital of the user, and
   a strap connecting to the head mounted portion,
   said head mounted portion having at least one closed curved belt,
   said closed curved belt having thereon at least one junction, at least one of the junctions provides the closed curved belt with a nonplanar structure adaptable to a shape of the head of the user,
   said junction being located neither at an intermediate position of said strap, nor an abutting position between said strap and said closed curved belt,
   wherein a part of said closed curved belt portion and said strap to be connected thereto are integrally formed by a Y-shaped member so that a plurality of said Y-shaped members are connected to each other to define the whole head gear.

2. A headgear according to claim 1 wherein said junction is formed by stitching.

3. A headgear according to claim 1 wherein further comprising at least two junctions that provide the nonplanar structure.

4. A headgear according to claim 3 wherein the number of said junctions in total is four.

5. A headgear according to claim 1 wherein said junction provides the nonplanar structure.

6. A headgear according to claim 1 wherein a sum of open angles of the junctions which provide the nonplanar structure is not less than 15 degrees.

7. A headgear according to claim 1 wherein said closed curve is generally circular, elliptical, or regular polygonal.

8. A headgear according to claim 1 wherein said strap connected to said head mounted portion comprises as many as five straps.

9. A headgear according to claim 1 wherein said strap connected to said head mounted portion comprises as many as four straps.

10. A headgear according to claim 9 wherein said straps include two straps of which a linear distance from a center of the closed curved belt to ends of the straps is 35 cm to 45 cm, and two straps of which a linear distance from the center of the closed curved belt to ends of the straps is 28 cm to 38 cm.

11. A headgear according to claim 1 wherein when it is worn on the user, the center of the closed curved belt lies in the vicinity of the opistocranion of the head of the user, and the area defined and surrounded by the closed curved belt is 50 $cm^2$ to 120 $cm^2$.

12. A headgear according to claim 1 wherein among the head mounted portion and the strap, at least the strap is made of a material that has a stretch of 0.05% to 20% when pulled at 1.96 N.

13. A method of manufacturing a headgear according to claim 1, the method comprising:
   a cutting off step to cut off a member forming a closed curved belt portion from a planar material, and
   a connecting step to connect at least one pair of a first cut end and a second cut end in the cut off member to form at least one junction, wherein, in said cutting off step,
   a series of members forming the closed curved belt portion are cut off from the planar material; at least one place of a portion of the series of members corresponding to the closed curved belt portion is cut off along a first cutting line, and is further cut off along a second cutting line which is in the proximity of the first cutting line and is not parallel with and does not intersect the first cutting line, to form said at least one pair of a first cut and a second cut end,
   or, each of the members forming said closed curved belt portion having said at least one pair of first cut end and second cut end is individually cut off from one or more planar materials.

14. A manufacturing method of a headgear according to claim 13 wherein in said cutting off step, said at least one pair of a first cut end and a second cut end are formed so that the sum of open angles of the first cut end and the second cut end is no less than 15 degrees when said member forming the closed curved belt portion lies in a plane.

* * * * *